United States Patent [19]

Friedman et al.

[11] Patent Number: 4,648,052
[45] Date of Patent: Mar. 3, 1987

[54] EYE-TRACKER COMMUNICATION SYSTEM

[75] Inventors: Mark B. Friedman; Gary J. Kiliany; Mark R. Dzmura, all of Pittsburgh, Pa.

[73] Assignee: Sentient Systems Technology, Inc., Pittsburgh, Pa.

[21] Appl. No.: 551,309

[22] Filed: Nov. 14, 1983

[51] Int. Cl.4 .................. G06F 15/28; H04N 7/18; A61B 3/14

[52] U.S. Cl. .................. 364/550; 364/415; 340/825.19; 340/365 P; 358/93; 351/210; 250/221

[58] Field of Search .................. 364/550, 415, 518; 351/205, 209, 210, 211; 358/93, 107; 340/825.19, 365 P; 250/221

[56] References Cited

U.S. PATENT DOCUMENTS

| | | | |
|---|---|---|---|
| 3,986,030 | 10/1976 | Teltscher | 351/210 X |
| 4,003,642 | 1/1977 | Vogeley | 351/210 |
| 4,075,657 | 2/1978 | Weinblatt | 351/210 X |
| 4,109,145 | 8/1978 | Graf | 340/825.19 X |
| 4,197,854 | 4/1980 | Kása | 364/415 X |
| 4,209,255 | 6/1980 | Heynau et al. | 358/93 X |
| 4,287,410 | 9/1981 | Crane et al. | 351/210 X |
| 4,387,974 | 6/1983 | Marshall et al. | 351/210 X |
| 4,494,838 | 1/1985 | Wallquist et al. | 351/205 X |
| 4,595,990 | 6/1986 | Garwin et al. | 364/518 |

FOREIGN PATENT DOCUMENTS 8123495 2/1983 United Kingdom ............... 351/209

OTHER PUBLICATIONS

Gauthier et al, "Two Dimensional Eye Movement Monitor for Clinical and Laboratory Recording", *Electroencephalography and Clinical Neurophysiology*, vol. 39, No. 3, pp. 285–291, Sep. 1975.

Video Signal Input, Robotics Age, Mar./Apr. 1981, pp. 2-11, 19.

Behavior Research Methods and Instrumentation; 1975, vol. 7(5), 397–429.

"Survey of Eye Movement Recording Methods", Young and Sheena, Journal of the Optical Society of America, vol. 48, No. 7, Jul. 1958.

"Eye Fixations Recorded on Changing Visual Scenes by the Television Eye-Marker", Laboratory Oculometer, NASA CR-1422, by John Merchant.

*Primary Examiner*—Errol A. Krass
*Assistant Examiner*—Joseph L. Dixon
*Attorney, Agent, or Firm*—Webb, Burden, Robinson & Webb

[57] ABSTRACT

A system for computer vision comprises a source of digitized video signals and a frame encoder circuit connected to the source of digitized video signals. The frame encoder encodes threshold crossing events at at least two threshold levels and stores encoded data for a two-dimensional area within the frame in a cache memory. The threshold levels are programmable. A computer is in communication with the encoder circuit at least via its data bus and address bus for programming the threshold levels and controlling the encoder and accessing the data in said cache memory. The computer has an associated main memory with a stored task for reading the cache memory and interactively controlling the frame encoder circuit and interpreting the data gathered thereby. Data is encoded by event type and pixel address wherein the event type is indicative of threshold crossed and direction of crossing. The task stored in main memory has an algorithm for continuously changing the threshold levels and analyzing the data in successive frames until the desired threshold levels are achieved.

2 Claims, 6 Drawing Figures

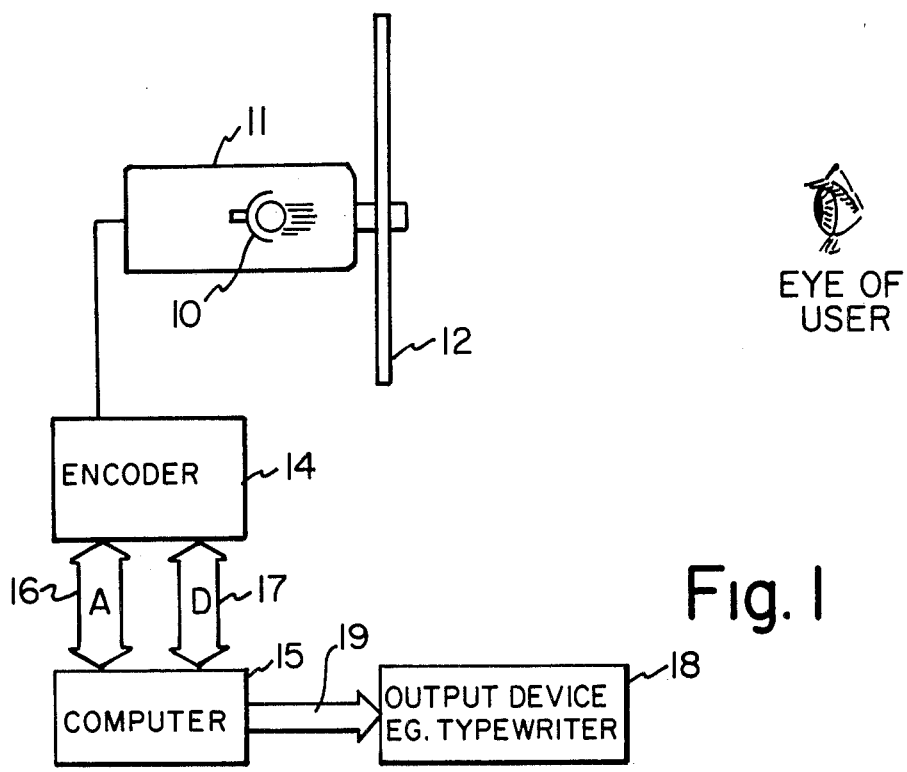

EYE-TRACKER COMMUNICATION SYSTEM

BACKGROUND OF THE INVENTION

Eye-trackers are instruments for measuring the movements of an eye. An eye-tracker communication system allows a physically handicapped person to use eye movements to communicate. There are several varieties as explained in "Survey of Eye Movement Recording Methods" by Young and Sheena, *Behavorial Research Methods Instrumentation*, 175, Vol. 7 (5), pages 397–429. A number of eye-tracking devices have been explained in the patent literature including U.S. Pat. Nos. 2,288,430; 2,445,787; 3,462,604; 3,514,193; 3,534,273; 3,583,794; 3,806,725; 3,864,030; 3,992,087; 4,003,642; 4,034,401; 4,075,657; 4,102,564; 4,145,122; 4,169,663; and 4,303,394.

One technique, the theory of which is explained in the Young and Sheena article, is the corneal reflection technique. The corneal reflection technique can be implemented in a number of ways. See, Laboratory Oculometer, NASA CR-1422 by John Merchant and "Eye Fixations Recorded on Changing Visual Sense by the Television Eye Marker" by Mackworth and Mackworth in *Journal of Optical Society of America*, Vol. 48, No. 7, July 1958.

While the prior art discloses eye-tracking devices, the applicants found that there was no relatively inexpensive eye-tracking system and technique which could be used by individuals on a more or less continual basis. Prior systems have been large and expensive, if adequate.

While it has been possible to use a digitized image processed by computer to implement the corneal reflection eye-tracking technique, it has required a very large, very fast computer to do so. Consider that a television frame divided into 240 lines by 256 pixels (picture elements) requires nearly 62,000 bytes of memory if one byte is stored for each pixel. Moreover, the time to load and compare and analyze 62,000 bytes of memory in a typical eight bit microprocessor would be no less than several seconds—too long for any value in a real time eye-tracking device.

Some form of digital preprocessing is essential if eight bit or even sixteen bit microprocessors clocked at typical rates are to be used in a practical eye-tracker. A preprocessing frame grabber is disclosed in "Video Signal Input" *Robotics Age*, March/April 1981, pages 2–11 and 19. The article describes a circuit for comparing video signals to an analog threshold (programmable at 256 levels) to establish one bit of data for each pixel and then packing the data (eight pixels to the byte) before dispatching each data byte one at a time to the associated computer memory. Eight thousand (8K) bytes of computer memory are required for one frame. Since only one bit of data for each pixel is gathered, a simple binary image is gathered which is insufficient for most computer vision applications. It is clearly insufficient for eye-tracking by the corneal reflection technique where it is necessary to locate the corneal reflection (the brightest location on the frame) and the pupil (either very dark or less bright than the corneal reflection). Moreover, eight thousand bytes (8K) of data is still a large quantity for real time processing. Consider that eye movements can take only fractions of a second.

SUMMARY OF THE INVENTION

Briefly, according to this invention, there is provided a system for computer vision comprising a television camera, a frame encoder circuit, and a computer having an associated main memory with a stored task. The television camera produces a video signal including synchronization signals. The frame encoder connected to the video signal from the camera encodes the signal at at least two threshold levels. The encoded data for a two-dimensional area within the frame, i.e., a window, is stored in a cache memory. The encoder circuit is provided with programmable threshold levels. The computer is in communication with the encoder circuit at least via its data bus and address bus. The task stored in the main memory of the computer reads the cache memory and interactively controls the frame encoder and interprets the data gathered thereby. According to a preferred embodiment, the frame encoder stores the data in the cache memory after first encoding the data by event type and pixel address. With two thresholds, four event types may be selected for recordation; namely, rising across or dropping across the upper threshold level and dropping across or rising across the lower threshold level. It is further preferable that the frame digitizer has a programmable data collection window within the frame such that the frame area within which data is gathered may be reduced by, say, one-twentieth. It is yet another preferred embodiment according to this invention that the frame digitizer have a programmable data collection rate wherein at least the precision of the horizontal pixel position may be doubled.

The task stored in main memory has an algorithm for continuously changing the threshold levels and analyzing the data in successive frames until desired threshold levels are established. The task stored in main memory may also have an algorithm for establishing the size and position of the data collection window based upon analysis of the data for the entire frame; for example, the frame might be positioned about the brightest spot on the frame. Preferably, the task stored in main memory has an algorithm for changing the data collection rate when the increased precision is feasible and useful.

One special embodiment of this invention comprises an eye-tracker system including a display, a light source, a television camera, a frame encoder, and a computer, said computer having an associated main memory stored with the task for establishing the vector from the center of the corneal reflection to the center of the pupil upon which the television camera is focussed. The television camera produces a video signal. The frame encoder is connected to the video signal output of the camera and encodes the signal at at least two threshold levels and stores the encoded data for the entire frame in a cache memory. The threshold levels are programmable. The computer is in communication with the encoder circuit at least via its data bus and address bus. The task stored in the main memory reads the cache memory and interactively controls the frame encoder. The task comprises a subtask for finding the corneal reflection of an eye upon which the camera is focussed by lowering the upper threshold until the brightest spot on the frame is detected. The task comprises a subtask for finding the pupil by raising the lower threshold until the border between the pupil and the iris is defined. The task has a third subtask for finding the center of the corneal reflection and the center of the pupil and establishing the vector (azimuth and length) from the center of the corneal reflection to the center of the pupil.

A specific embodiment according to this invention comprises an eye-typer. The apparatus for the eye-typer comprises the above described eye-tracker apparatus and a display board bearing indica, for example, the characters of the alphabet plus punctuation and control characters. The display is arranged with the light source and television camera facing through it and away from it. The computer then has another task stored in main memory which calls upon the tasks already described. This additional task associates vectors of the corneal reflection with the character on the display board which is being looked upon by the user of the eye-typer. Characters can, thereby, be selected and sent to the output device, for example, a typewriter.

THE DRAWINGS

Further features and other objects and advantages of this invention will be clear from the followng detailed description made with reference to the drawings in which FIG. 1 is an overall schematic of an eye-tracker system;

FIG. 2 is a view of a display which might be used with an eye-typer system;

DESCRIPTION OF THE PREFERRED EMBODIMENTS

Figure 3:
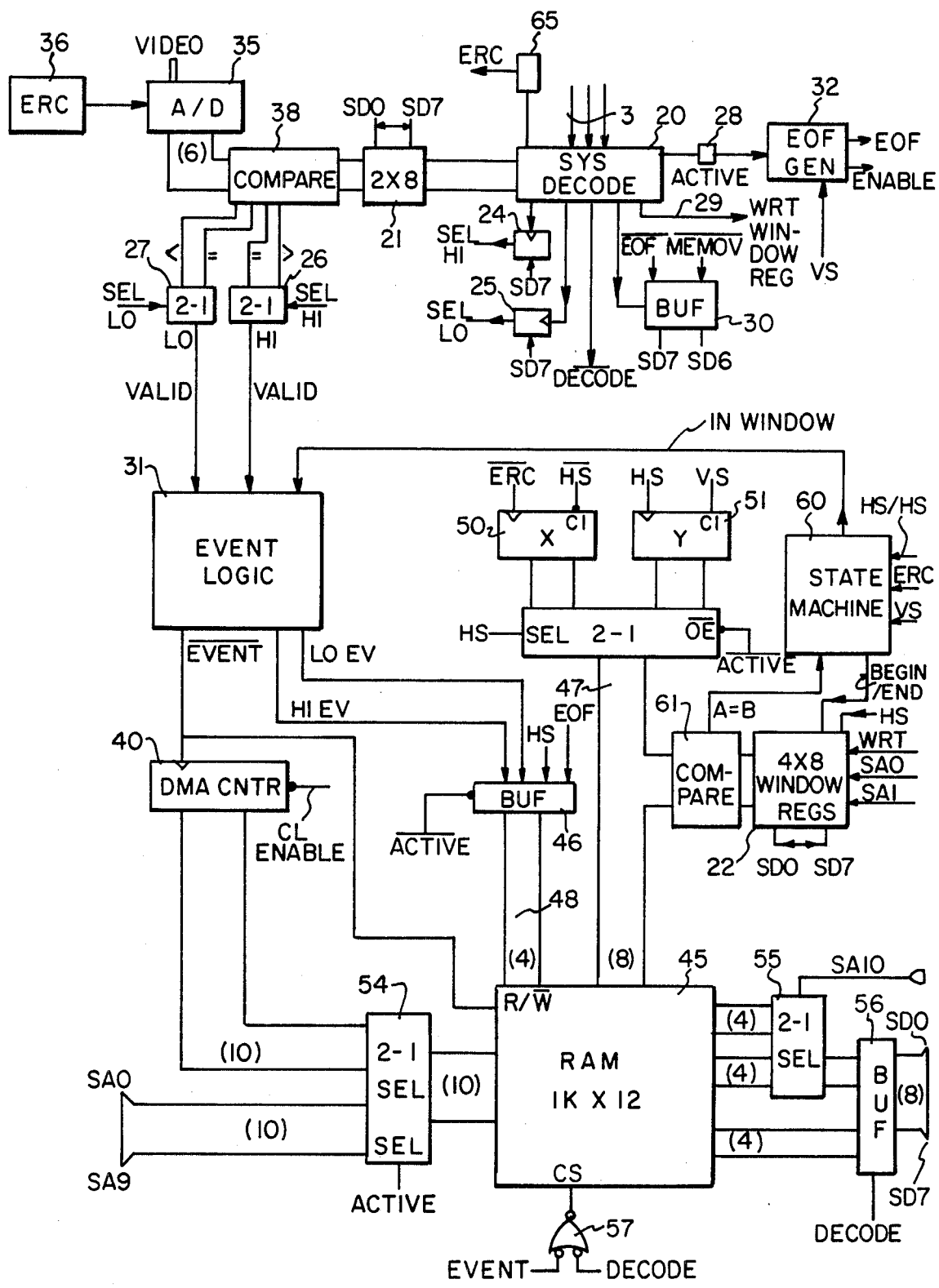
FIG. 3 is a function level circuit diagram of a frame encoder useful with the system of this invention.

Referring now to FIG. 1, the overall system for an eye-tracker according to this invention is set forth. The system includes a light source 10 (which may be an infrared light source) and a television camera 11 (which must, of course, be an infrared sensitive television camera if the light source is infrared). The light from the light source 10 is beamed through an opening in the display board 12 before which the user sits. The sight of the camera 11 is also through the opening in the display board. A display board suitable for use with the eye-tracker as an eye-tracker is shown in FIG. 2. The user, sitting before the eye-typer can select a letter by looking at it for a predefined period of time. The remainder of the system analyzes the video image of the eye to determine at what letter the eye is gazing and signals a typewriter or printer or the like to type that letter. Other applications of the eye-tracker are contemplated by this disclosure, for example, telephone dialers, machine controls, speech generators and the like.

The display has about 30 characters spaced about the center of the display. The number of characters that can be placed upon the display is directly related to the precision with which the corneal reflection vector is established. For a given data rate (say 256 pixels 240 lines) the precision is dependent upon the extent to which the pupil falls within the frame and the precision with which the centers of the pupil and the corneal reflection can be determined. The extent to which the pupil falls within the frame involves a trade-off. Head movement (side-to-side or up-and-down) can only be tolerated by having the pupil fall within the frame no matter the head position. Allowing for greater head movement requires giving up corneal vector precision. (The image of the pupil on the frame must be smaller for increased head movement). Applicants have chosen to provide head movement in the range of two to three inches and a display of about 30 characters as a satisfactory compromise. This compromise can only be made because of the accuracy with which the edges of the corneal reflection and pupil are obtained by the entire system discloed herein. Thus, the quality of the data gathered by the eye-tracker is critical. The quantity available from solid-state cameras having a digitized output has not to data been found satisfactory.

Referring now to FIG. 3, the encoder circuit comprises a number of programmable registers for configuring the circuit and at least one readable register for providing status information. Two eight-bit registers 21 are provided to hold the upper and lower threshold values. (In the embodiment described only six bits of these registers are actually used as the analog signal is only digitized at sixty-four levels.) Four more eight-bit registers 22 are required to hold the X and Y counts (frame addresses) of two corners (upper left and lower right) of the window within which the data is collected. The entire frame may fall within this window. Several one-bit registers (latches) hold control data. Register 24 holds the select high flag and register 25 holds the select low flag. These are applied respectively to select the high valid gate 26 and the low valid gate 27; which gates control flow of information to the event logic 31. A one-bit control register 28 holds the "active" flag which places the encoder circuit in the data collection mode. The output of a decoder 29 presents the "write to window register" flag which is set true during the time data is being written to the window registers. The system decode logic 20 generates a board select signal ("$\overline{\text{decode}}$") from the signals on the address bus of the associated computer and specifically points to the control registers 21, 24, 25, 28, and 30. It is also used to generate the output of decoder 29.

One status register 30 may be read and contains at least two bits of status of information; namely, and end of field ("$\overline{\text{eof}}$") flag and a memory overflow ("$\overline{\text{mem ov}}$") flag. The output of the control register 28 holding the active flag is applied to the end of file (EOF) generator 32 which also has applied thereto the vertical sync (VS) signal of the video signal. The EOF generator 32 looks for the negative edge of the vertical sync signal next following the change of the active flag to start the "enable" signal. The enable signal remains high or true during the whole field. The "EOF" output of the EOF generator goes active at the end of the frame just captured. These signals are used to control the data gathering process.

The video input to the encoder circuit is continually digitized by a six-bit analog to digital (A/D) converter 35 which is clocked by an element rate clock (ERC) 36. (With a digital camera of sufficient quality, should one become available, the television camera output signal would not be analog and the analog-to-digital apparatus on the encoder board would be eliminated. The output of the digital camera would then be applied to the dual digital comparator circuit 38.)

The clock 36 is free running and is gated to the converter 35 by the vertical sync and horizontal sync signals. The element rate clock outputs a clock pulse at about five megahertz under typical conditions. This permits the gathering of approximately 256 pixels per line. The output of the A/D converter is continually applied to a dual digital comparator circuit 38 comprising two comparators. To one side of the first comparator is applied the upper threshold level; to one side of the other comparator is applied lower threshold level. The output from the upper comparator is an equal to or greater than signal. The output from the lower comparator is an equal to or less than signal. These signals are applied via the high valid and low valid gates 26, 27 to the event logic 31.

The encoding scheme for the digitized data will now be explained. Run length encoding is a data collection scheme in which only the time between events is stored. Applicants' encoding scheme is a significant departure from run length encoding. The X address of a pixel for which an event is detected is stored with the data descriptive of that event. The twelve-bit word which is stored for such an event comprises eight bits of X address data and four bits of type data. At the end of every line in which an event takes place, the Y address of the entire line is stored. The bit length of each data word including event and event type must, of course, exceed eight, where the address count is 256 or more. The particular implementation described herein stores six types of events and could thus be encoded in three bits, but as a practical matter stores the information about the six event types in four bits. The six types of events encoded, according to the specific embodiment disclosed, are (1) rising oven (begin) high threshold;
(2) dropping through (end) high threshold;
(3) dropping through (begin) low threshold;
(4) rising through (end) low threshold;
(5) end of line (Y address follows); and
(6) end of frame.

The applicants have found that the encoded data required for properly tracking an eye can be stored in a 1K (1024) by twelve-bit word cache memory 45. Note that the exact amount of memory required depends upon the number of events encountered. The data so summarized can be easily analyzed by the task stored in the main memory of the associated computer during real time processing.

The event logic 31 outputs an "$\overline{\text{event}}$" signal every time the upper or lower threshold is crossed unless the "in window" input disables all outputs of the event logic. The event logic signal is applied to clock the DMA counter 40 for the cache memory 45 and is also applied to the R/$\overline{\text{W}}$ input of the cache memory to permit the contents of the event buffer 46 and the X or Y counter bus 47 to be written to the cache memory. Two other outputs of the event logic are the low event (LoEv) and high event (HiEv) lines which encode the event type relating to threshold crossings.

The event buffer 46 is a four-bit buffer which writes to the high order bits in the cache memory. Two bits are binary coded to indicate one of four types of events and two other bits are flags, one to note horizontal sync (HS) (end of line) and the other to indicate end of the frame (EOF).

The X and Y counters 50 and 51 are eight bit counters. The X counter (pixel counter) is clocked by the inverted output of the element rate clock ($\overline{\text{ERC}}$) and is reset by the fall of the horizontal sync signal ($\overline{\text{HS}}$). The Y counter (line counter) is clocked by the horizontal sync signal ($\overline{\text{HS}}$) and is reset by the rising edge of the vertical sync signal (VS). An eight-bit, two bus input multiplexer 53 multiplexes the outputs of the X counter and Y counter to the eight-bit X or Y counter bus 47. The multiplexing signal is the horizontal sync signal ($\overline{\text{HS}}$) which causes the Y counter data to flow to the bus 47 at the end of a line. Otherwise, the X counter data flows to the bus 47.

The "active" signal, that is, the output of register 28 is not only applied to the EOF generator. It is inverted and applied to the X-Y address multiplexer 53 and the event buffer 46 to place them in the high impedance state such that they are isolated from the buses 47 and 48 and the cache memory 45. This enables the use of these buses for reading the contents of the cache memory to the computer. The active signal also selects the cache memory address multiplexer 54 to pass the event address generated by the DMA counter 40. Otherwise, the address bus of the computer has access to the cache memory.

The cache memory 45 is written to at the time of an event. At that time the next free address in the cache memory is placed upon the memory address bus by the DMA counter 40 and the cache memory address multiplexer 54. The $\overline{\text{event}}$ signal out from the event logic clocks the DMA counter and sets the R/$\overline{\text{W}}$ of the cache memory to the write condition. The $\overline{\text{event}}$ signal also strobes the chip select (CS) input to the cache memory through NOR gate 57. Each word of the cache memory must be read in two steps when the computer data bus is only eight bits wide. The four bits of type data must be multiplexed by memory output multiplexer 55 which is selected by line SA10 of the computer address bus in the embodiment disclosed. The multiplexed output of the cache memory is buffered from the computer data bus by the buffer driver 56 which is activated to pass the cache memory data upon application of the $\overline{\text{decode}}$ signal. The $\overline{\text{decode}}$ signal is also NORed at 57 with the $\overline{\text{event}}$ signal to strobe the chip select (CS) input to the cache memory during a memory read.

The window logic comprises a state machine 60, digital comparator 61, and the four window address registers 22. One of the four address registers is placed on one side of the comparator 61 according to the following selecting inputs:

| Register | Input | Input |
| --- | --- | --- |
| Vertical Begin | Begin | HS |
| Vertical End | $\overline{\text{Begin}}$ | HS |
| Horizontal Begin | Begin | $\overline{\text{HS}}$ |
| Horizontal End | $\overline{\text{Begin}}$ | $\overline{\text{HS}}$ |

The data bus 47 places the current X or Y count upon the other side of the comparator 61 depending upon whether the HS or $\overline{\text{HS}}$ is applied to the X-Y address multiplexer 53. The output of the comparator is a true or "matched" signal when a match is found.

The inputs to the state machine are the HS/$\overline{\text{HS}}$, ERC, $\overline{\text{VS}}$, and "matched" signals. The outputs are the "in window" and "begin" signals. The state machine has flags "vertical in" and "horizontal in" which, when both set true put the "in window" in the true state. (State to enable the event logic 31.)

At the time of the horizontal sync preceding the first line, the vertical in and horizontal in flags are set false and the begin address flag which controls the begin output, is set true. When a match is found for the vertical begin, the vertical end flag is set true and the begin address flag remains true. Now the state machine looks for a begin X address and when found, sets the horizontal in flag true and therefore the window in output true. The begin flag is set false. The state machine now looks for the next end address (the begin flag being set false). If an end address match is found (either X or Y count) the flags are set accordingly. If an X end match is found, the begin flag is not set false but left to look for the Y end match during the next horizontal retrace. At the start of every line, the begin flag is set true so that the state machine can find the begin X address match for that line.

Figure 4:
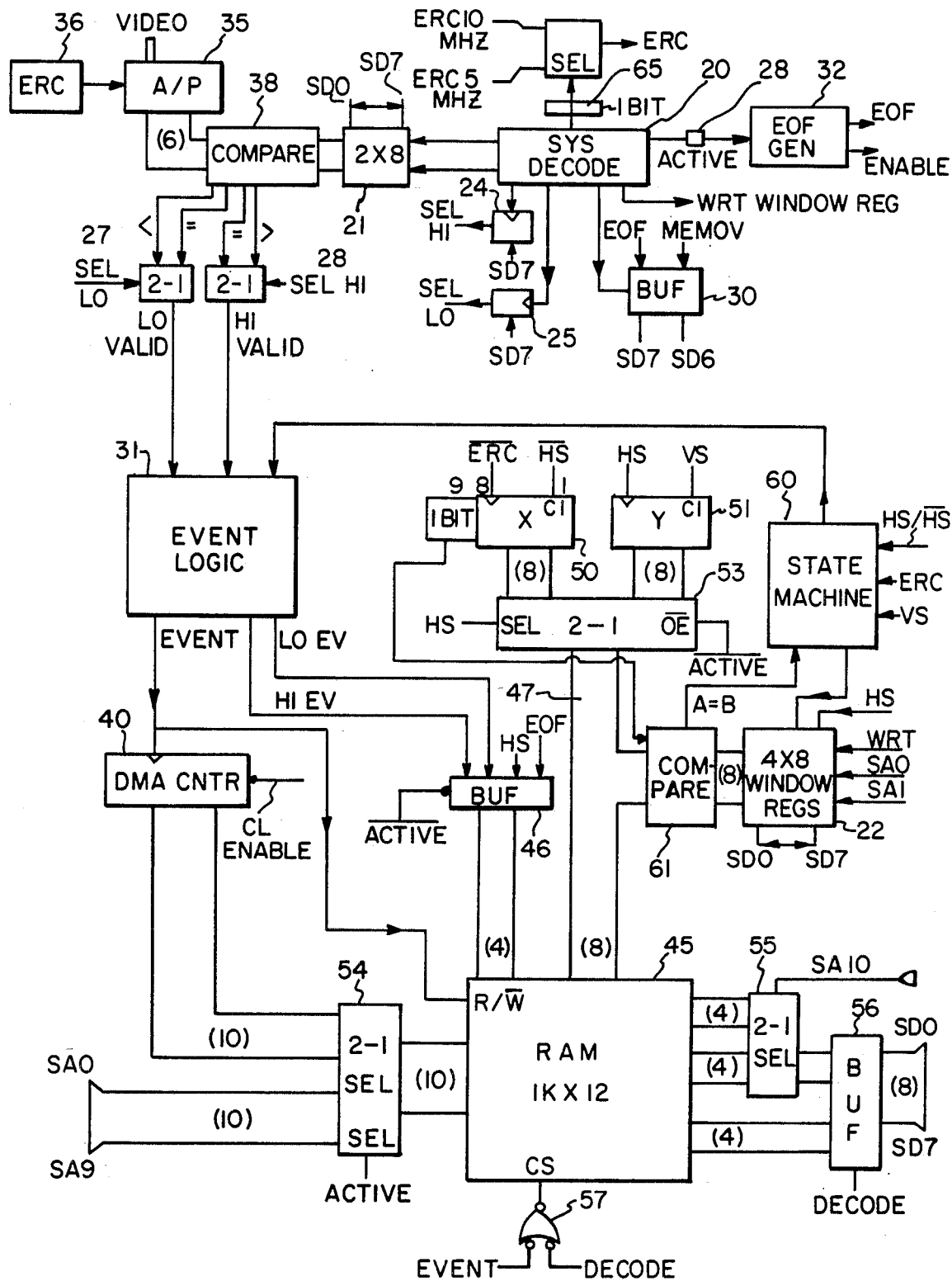
FIG. 4 is similar to FIG. 3 and illustrates an embodiment wherein the data collection rate is programmable.

According to a preferred embodiment shown in FIG. 4, the element rate clock is programmable by a one-bit register 65 so that it either clocks at five megahertz (the normal situation) or ten megahertz. According to this embodiment, the X counter must be enlarged to count an additional bit. The connection between the data bus 47 and the comparator circuit 61 is rewired to shift the input down so that the high order seven bits on the bus 47 are applied to the low order seven bits of the comparator input. (This shift has the effect of dividing the count by two prior to applying to the comparator.) The output of the ninth bit in the counter is applied directly to the high order bit of the comparator input. It will be zero during the HS pulse so as not to disturb the divided Y-count applied to the comparator. The frame addresses are stored in the window register after first dividing by two except the X count during the ten megahertz rate.

Figure 5:
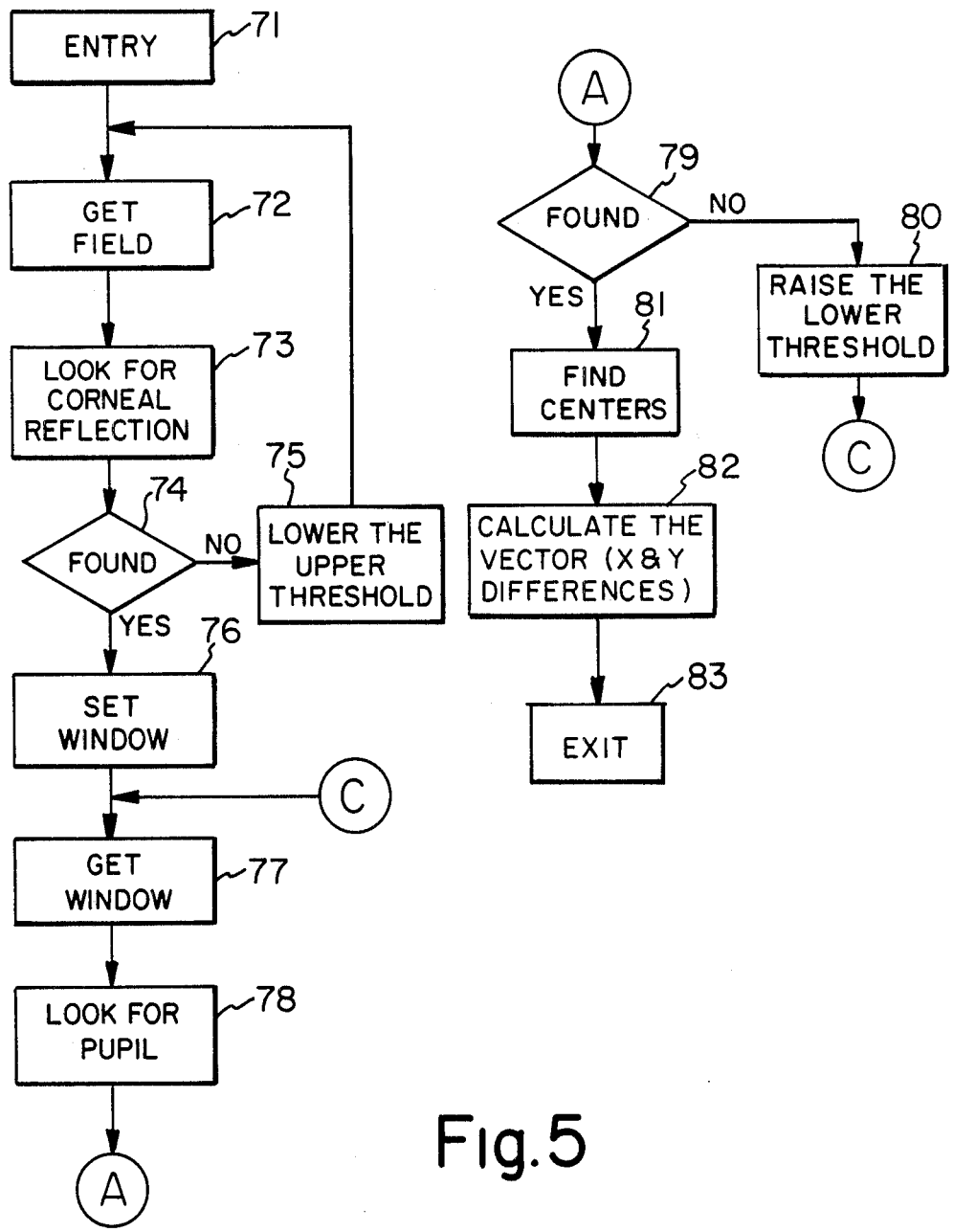
FIG. 5 is a flow diagram showing the task for detecting the azimuth direction of the gaze of the eye upon which the system is focussed.

Referring now to FIG. 5, there is shown a flow diagram of the portion of the software or task in the computer main memory which most directly interfaces with the encoder circuit. The entry point at 71 leads to 72 in which the encoder circuit is instructed to grab a field. Thereafter at 73 the data in the cache memory is reviewed looking for a corneal reflection; that is, the very brightest spot on the frame. If, at 74, a bright spot is found control moves to 76 at which the window size is set about the corneal reflection. However, if no corneal reflection is found, the upper threshold is lowered at 75 and an additional field is grabbed. After the window is set at 76 the data for the window is grabbed at 77 and thereafter the computer looks at the data in the cache memory to find a pupil at 78; that is, a dark round spot near the corneal reflection. If no pupil is found, at 79 then the lower threshold is raised at 80 and an additional window is grabbed until a pupil is found. When a pupil is found, control passes to 81 where an algorithm finds the centers of the pupil and center of the corneal reflection and then control is passed to 82 where the vector between the centers is calculated. Exit to the main program is at block 83 where the vector is correlated with a particular indicia upon the display and an output indicative of the indicia selected is made.

The pattern recognition techniques used for establishing that either the corneal reflection or the pupil has been found are variations of standard pattern recognition techniques. If, during the procedure at 73, the first byte of information stored in the cache memory is an end of field indication, then no corneal reflection has been found and the upper threshold must be lowered. (During this time, the lower threshold is set so that it will not produce any event.) When event data first appears in the cache memory following frame grab, a test is made to determine that all event data is related to substantially contiguous pixels on successive lines indicative of only one bright spot. If more than one bright spot is detected, the shape of the spots are considered and the spot that is closest to round is taken as the corneal reflection.

The pattern recognition technique used for finding the pupil during the procedure at 78 is somewhat more complex. As the lower threshold is raised, events begin to appear in the cache memory. A test is made to determine that they are in substantially continguous pixels in adjacent lines which is indicative of one dark object being detected. If more than one dark object is detected (for example, the eyebrow is also detected) the most circular object is taken as the pupil. The lower level is raised even after the pupil is first detected. With successive increases in the lower threshold level the size of the detected pupil will increase until a "dead zone" is reached in which increase in the lower threshold level produces very little increase in the size of the pupil. At this time, raising of the lower threshold is stopped and the pupil is considered found.

The procedure for detecting the center of the corneal reflection and the pupil are variations of standard techniques. An obvious difficulty with detecting the center of the pupil is that the corneal reflection often has removed a portion thereof.

Assembly language source code for the procedures set forth in FIG. 5 is provided at the end of this specification.

Figure 6:
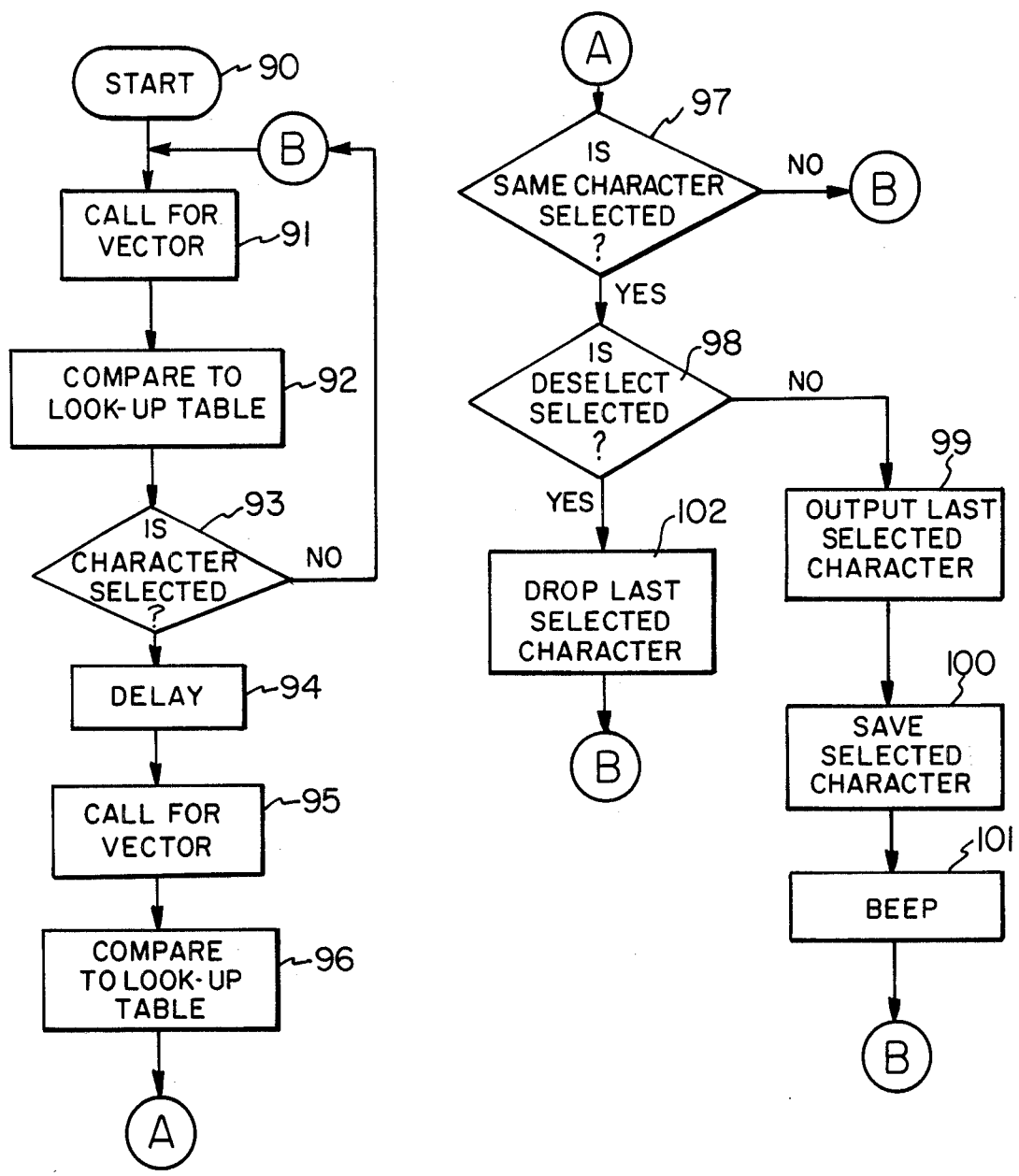
FIG. 6 is a flow diagram showing a task for associating corneal reflection vectors with characters and outputting characters to a display device.

Referring to FIG. 6, there is shown a flow diagram of a task for associating corneal vectors with characters. The corneal vectors are previously associated with each character position on the display by a trial and error procedure and are stored in a look-up table. By and large, the curvature of the corneas of most human eyes are sufficiently similar so that only one table need be established. Of course, the table associates ranges of X differences (differences in the X address of the centers of the corneal reflection and the pupil) and ranges of Y differences with each character positioned. Storing ranges provides the ability to work with the eye of more than one individual under differing conditions.

It should be understood tht any number of equivalent tasks could be developed within the scope of this invention to correlate the corneal vectors and the desired outputs. From the start 90 (FIG. 6), the task moves to a call for a vector at 91 which is a call to the task described with reference to FIG. 5, for example. The vector returned by the call (in terms of X and Y differences) is then compared to the predefined look-up table at 92. At 93, a test is made to determine if the vector corresponds to a character in the look-up table. If not, control is returned to 91 and another vector is sought. If the vector corresponds to a character, it is considered initially selected. After a delay at 94, another vector is obtained and compared to the look-up table at 95 and 96. If the same character is not selected as was initially selected, the process starts over. If the same character is selected at 97 it is considered firmly selected and will be output if not deselected. At 98, a test for the deselect character is made. If the deselect character has not been chosen, the last firmly selected character is output at 99 and the just selected character is saved at 100. Preferably, a feedback signal indicating selection, for example, a beep is output at 101. If the deselected character has been chosen, the last selected character is dropped. Following either save of a firmly selected character or deselect, the task starts all over again looking for the next selection.

```
** Macro Imports **

.mcall RESET, INCR, ADDB, MOVI, MOV, BRA, PAUSE
      .mcall CALL

RESET AIM          ; set things up nicely for AIM-65

.USES Speech
      .mcall [Speech] DM.BELL, DM.WAIT

Pseudo Register Allocation r0 - pointer to next data byte of frame data
      r1 - pointer to next status byte of frame data r2 - (pass1) XSum - sum of x values
           (pass2) Ysum - sum of y values of lines with filtered data r3 - (pass1) YSum - sum of y values
      r3 - (pass2) hi level x sums r4 - (pass1)
      r4 - (pass2) holds 16 bit running sum of midline values r5 - (pass2) temporary
      r6 - (pass2) Y difference    , XDifference

** Global Constants **

.iif ndf,isPROM,start   = $0c00
      .iif df,isPROM,start    = $c000 escyes == $AA     ; used for escape key polling control
      page0 = $98

** Video Image Processor Registers **
      These registers are write only.

HiReg   = $9800  ; hi level threshold reg
      LoReg   = $9900  ; lo level threshold reg
      Enabl   = $9b00  ; enables the video processor
      Disabl  = $9c00  ; disables the video processor
      VIPSta  = $9d00  ; VIP status
      LoComp  = $9e00  ; Lo threshold comparator configuration
      HiComp  = $9f00  ; Hi Threshold comparator configuration
      BoxXB   = $9a02  ; Box X Begin
      BoxXE   = $9a00  ; Box X End
      BoxYB   = $9a03  ; Box Y Begin
      BoxYE   = $9a01  ; Box Y End

** Internal Constants **

HiDec  = 1      ; constant for decrementing hi lev threshold
        MinHi  = 55     ; minimum hi level
  sigh  MxCorH = 06     ; maximum cornea spot height
  sigh  MxCorW = 06     ; maximum cornea spot width XRect  = 30     ; 2 * XRect is width of box
        YRect  = 50     ; YRect + 25 is height of box LoInc  = 1      ; used to increment lo register
        IniLo  = 7      ; used in drawbox- sets initial loReg value for pass2
        MaxLo  = 20     ; maximum value of the lo register Limit  = 1      ; # of times user must be looking at a display region
        filter = 2      ; only look at lines wider than filter (Lo Pass filter)
```

```
        XMidFilt= 6       ; second Lo Pass filter (after cornea fill in)
        StopVal = $10     ; counts needed to decide to stop ramping LoReg

**** The following constants define the boundaries for x and y criteria
     for each word position. ****

TyGrt = $08       ; lower top y boundary
        TyLss = $15       ; upper top bndry
        ByGrt = $00       ; bottom y stuff
        ByLss = $02       ; ...
        MidGrt = 03
        MidLss = 06

LftGrt = $F3      ; leftmost boundary
        LftLss = $FB      ; inner lft bndry
        RgtGrt = $06      ; inner right bndry
        RgtLss = $12      ; rightmost boundary
        MidLft = $02      ; middle word position, leftmost boundary IniHi = $40       ; initial value of Hi level register
;  Page Zero Definitions 
;
        . = $30
FHiReg : . = . + 1         ; Fake Hi Reg - needed because hireg write only
FLoReg : . = . + 1         ; Fake Lo Reg
numx   : . = . + 1         ; Pass1 - number of x values used to find center
xcen   : . = . + 1         ; Pass1 - x center of cornea spot
ycen   : . = . + 1         ; Pass1 - "y center" of cornea spot
flag   : . = . + 1         ; Pass1 - MSB used to tell endfram that spots in frame
xstat  : . = . + 1         ; pass1
tmp    : . = . + 1         ; pass1
PrevLo : . = . + 1         ; Dynamic LoReg hacking; maintains state between grabs
;
;********
Lodiv  : . = . + 1         ; lo byte of dividend for divide routine
Result : . = . + 1         ; result of 16bit by 8bit division
Divisor: . = . + 1         ; divisor for divide routine
;
state  : . = . + 1         ; holds the state of the pass2 processing
Ystat  : . = . + 1         ; holds the status of the y scan line
Ytemp  : . = . + 1         ; holds temporary y value for pass2 and pass1
vector : . = . + 2         ; holds vector for indexing into pass2 jump table
;
errcnt : . = . + 1         ; holds number of digitizer data errors
;
TmpXB  : . = . + 1         ; temporary x begin
TmpXE  : . = . + 1         ; temporary x end
LXend  : . = . + 1         ; filtered x end value
;
YcntHi : . = . + 1         ; holds number of lines with hi lev on it
FstBg  : . = . + 1         ; holds first LoBg value on a line
;
stack  : . = . + 1         ;hack used in divide
;
BXetmp : . = . + 1         ; Box Xend temporary ( boxxe write only reg )
BxBtmp : . = . + 1         ; Box X Begin Temp
YBxBtmp: . = . + 1         ; Box Y begin temp
YBxEtmp: . = . + 1         ; Box Y end temp
oldY   : . = . + 1         ; holds last y val processed by Eol2
EntCnt : . = . + 1         ; counts number of times enter2 is called
;
YHiBg  : . = . + 1         ; Holds y pos of first line with hi lev data on it
YcntLo : . = . + 1         ; holds number of lines with lo lev on it
widcnt : . = . + 1
widstat: . = . + 1
;
LimCnt : . = . + 1         ; limit count
PrevVal: . = . + 1         ; previous value returned from the eyetracker !!
```

```
;
PrevCor: . = . + 1        ; computed in drawbox (=FHiReg+HiDec)
;this is used so that the next sample knows what hireg val the previous
; sample stopped at.
;
HTmpXB: . = . + 1         ; used in pass2 Hi lev x beg
HtmpXE: . = . + 1         ; same ... Hi Lev x end
HYtmp : . = . + 1         ; used in eol2 (cornea streaking check) hi y temp
;
PupYCen:. = . + 1         ; pupil y center
PupXCen:. = . + 1         ; pupil x center
CorXCen:. = . + 1         ; cornea x center
CorYCen:. = . + 1         ; cornea Y center
;
Escape: . = . + 1         ; MD: escape key pressed if bit 7 is true
XavgBase:. = . + 15
YavgBase:. = . + 15
;
        . = page0
AvgPntr:. = . + 1
; ****************************************************************
;
        . = Start
;
;mainf: jsr ETrack         ; this is a test
;       txa                ; push word position on stack
;       sta r9
;;      Call CrLf
;       lda r9
;       cmp #escyes
;       beq monfoo
;       Call NumOut        ;  and print it
;       BRA mainf          ; THEN play it again sam !
;monfoo:        jmp mon    ; jump to monitor because escape pressed
;
;------------------------------------------------------------
;
ET.init::
        lda #00
        sta AvgPntr        ; pointer to next location in circular buffer
        rts
;
ETrack::lda #0
        sta LimCnt         ; zero limcnt
        sta PrevVal
;
        lda #IniHi         ; initial hi reg value
        sta PrevCor        ;   Initialize PrevCor value
;
enter3: jsr begin          ; eyetrack !!!!!
;
        bit Escape
        bpl go.80
;
ret.5:  ldx #escyes        ; put something in x that indicates do not say a word
        rts
;
go.80:;
        cpx #$FF
        bne saywrd         ; IF a valid eye gaze position THEN say wrd
        jmp enter3         ; ELSE grab another eye
;
SayWrd:
ret.1:  rts     ; return with eye gaze position in Xreg
;
;
; this one computes a running average of the x and y diffs and
; numouts them.
```

```
;
        avglength = 5           ; length of running average buffer
;
AvgRun:;
AvgTop:  jsr top                ; get a x and y diff
         beq Avg.11             ; return if an escape was pressed
;
         lda r6                 ; y diff
         ldx AvgPntr
         sta Yavgbase,x         ; store y diff in buffer
         lda r6+1
         sta XavgBase,x         ; store x diff in buffer
;
         jsr compAvg            ; compute the average of the buffers and numout them
;
         inc AvgPntr            ; inc pointer into circular buffer
         lda AvgPntr
         cmp #Avglength
         bne avg.10
;
         lda #00                ; close the circle in the circular buffers
         sta AvgPntr            ; i.e. reset pointer to the beginning of the buffers
;
Avg.10:  lda #$FF               ; hack to zero Z flag indicating no esc key pressed
Avg.11:  rts
;
; CompAvg - computes the average of the x and y diff circular buffers
;
;
CompAvg:MOVI 0,r2
         ldx #00
;
avg.1:   lda YAvgBase,x         ; get a y val
         clc
         adc r2
         sta r2
         bcc avg.15
         inc r2+1
;
avg.15:  inx
         cpx #AvgLength
         bne avg.1
;
         lda #00
         sta result
         lda #AvgLength
         sta divisor
         lda r2
         sta LoDiv
         lda r2+1
         jsr divide             ; divide r2 by AvgLength (length of circ buffer)
;
;        Call Blank2            ; print two blanks to the tty
         lda result
;        Call Numout            ; write avg y diffs to the tty
         sta r6                 ; store ydiff run averaged at r6
;#####
         ldx #00
         MOVI 0,r2
;
avg.2:   lda XAvgBAse,x         ; get an x diff
         sta r5
;
; now add Ac to r2, sign-extended
;
         clc
         adc r2
         sta r2
```

```
;
        bcc avg.3
        bit r5
        bmi loopend
        inc r2+1
        bra loopend
;
avg.3:  bit r5
        bpl loopend
        dec r2+1
;
loopend:inx
        cpx #AvgLength
        bne avg.2       ; add more nums to the running sum
;
;now compute the average (do the division)
;
        bit r2+1        ; see if negative
        php             ; save the sign
        bpl isPos
;
; complement r2 -> perform src := 65536 - src !!
;
        jsr cpl
;
; now actually do the sixteen bit by eight bit divide
;
isPos:  lda #0          ; zero result
        sta result
        lda #AvgLength  ; setup divisor
        sta Divisor
        lda r2          ; put lo byte of dividend in LoDiv
        sta LoDiv
        lda r2+1        ; put hi byte of dividend in Ac
        jsr Divide      ; go for it!
;
; see if result is negative
;
        plp
        bpl NOut
;
; yes -> 8-bit complement
;
        sec
        lda #0
        sbc Result
        sta Result
;
NOut:;  call Blank2
        lda Result
        sta r6+1        ; store run length averaged x diff at r6+1
;       call NumOut
        rts
;
begin:  jsr AvgRun
        beq ret         ; esc key pressed so return
;
go.30:  lda r6          ; ydif
        cmp #TyGrt      ;top y boundary
        bcs topQ        ; looking at top ?
        cmp #MidGrt
        bcs MidY        ; middle (y dim) words
        cmp #ByGrt      ;bottom y boundary
        bcs botQ        ; looking at bottom ?
        ldx #$FF
        clc
ret:    rts
```

```
;
TopQ:   cmp #TyLss      ;tylss
        bcc TopYes      ; user looking at top level of display
        ldx #$FF
        clc
        rts
;
TopYes: jsr XCheck      ; check xdifs now
        tax
        rts
;
MidY:   cmp #MidLss
        bcc MidYes
        ldx #$FF
        rts
;
MidYes: jsr xcheck
        cmp #$FF
        beq nowrd
        cmp #00
        beq mid.1
        cmp #02
        beq mid.2
        ldx #$FF
        rts
mid.1:  ldx #$03
        rts
mid.2:  ldx #$04
        rts
;
BotQ:   cmp #ByLss
        bcc BotYes      ; user looking at the bottom display area
        ldx #$FF
        rts
;
BotYes: jsr XCHeck
        cmp #$FF
        beq NoWrd
        clc
        adc #$05        ; add 5 to what XCHeck returns because this is the
        tax             ;   bottom line
        rts
;
NoWrd:  ldx #$FF
        clc
        rts
;
;       find out what word in x dimension the user is looking at
;
XCheck: lda r6+1        ; x dif
        cmp #LftGrt
        bcs lftQ
        cmp #RgtGrt
        bcs rgtQ
        cmp #00
        bcs MidQ
        lda #$FF
        rts
;
lftQ:   cmp #LftLss
        bcc lftwrd
        beq lftwrd
        lda #$FF
        rts
;
lftwrd: lda #$00        ; put a 1 in A and return indicating looking at
        rts             ;       left word
```

```
;
MidQ:      cmp #MidLft      ; middle word position left boundary
           bcc MidWrd
           lda #$FF
           rts
;
MidWrd:    lda #$01         ; MidWrd indicated by a 2 in Ac
           rts
;
;
rgtQ:      cmp #$FE
           beq MidWrd       ; If x diff = FE then Middle pos
           cmp #$FF         ; If X diff = FF then Middle Pos
           beq MidWrd
           cmp #RgtLss
           bcc rgtwrd
           lda #$FF
           rts
;
Rgtwrd:    lda #$02         ; put a 2 in A indicating looking at a right word
           rts              ;                                      position
;
;
; *************************************************************
;
top:       lda #IniHi       ; initial Hi Reg value
           sta PrevCor      ; store at Prevcor (start <at max value of Hi reg
;                                            for the ramp down)
;          this code checks if the esc key is pressed:
;                   if esc is pressed, Z is true.
;                   if esc is not pressed, Z is false.
;
;          Thus, Z = (esc key pressed)
;
;          RAM/IO Timer module addresses
;
           RIOT.A  = $a480
           RIOT.B  = $a482
           EscRow  = %11111011    ; esc key row bit
           EscCol  = %10000000    ; esc key col bit
;
top.1:
TstEsc:    clc              ;
           ror Escape
           lda #EscRow      ; load row pattern to check esc key
           sta RIOT.A       ; write to RIOT kbd output reg
           lda RIOT.B       ; read RIOT kbd input reg
           and #EscCol      ; see if col pattern is esc key
           bne top.2
           sec
           ror Escape
           rts
;
;
top.2:     sta disabl       ; make sure VIP is disabled
           cld              ; clear decimal mode
;
           lda #0           ; init error count
           sta errcnt
;
           lda #$0A
           sta BoxXb        ; init box x begin
           lda #$05
           sta BoxYb        ; init box y begin
;
           lda #00
           sta LoReg        ; init lo reg
           sta FLoReg       ; must maintain internal copy - LoReg write only
```

```
;
        lda #$FE
        sta BoxXE        ; init box x end
        lda #$e0
        sta BoxYE        ; init box y end
;
        lda #$ff
        sta LoComp       ; set up Lo lev comparator for A < B
        sta HiComp       ; set up Hi Lev comparator for A > B
;
        lda PrevCor      ; get hi reg val computed on previous sample
;                                (unless top was the entry point)
        sta HiReg        ; init Hi reg
        sta FHiReg       ; internal copy - HiReg write only
;
Pass1:  sec              ; set carry
        lda FHiReg       ; load internal copy of hi reg
        sbc #HiDec       ; decrement hi lev
        cmp #MinHi       ; hi lev reg too low ?
        bcs cont         ; no ---> continue
        lda #IniLo       ; yes ---> start over
        sta PrevLo
        jmp top
;
cont:   sta HiReg        ; put new hi lev value in hi reg
        sta FHiReg       ; and in internal copy
;
        lda #00
        sta numx         ; number of x vals used to find cornea x cen
        sta flag         ; MSB tells endfram if data in frame or not
        sta oldy         ; previous y val of line with data on it
        sta xstat
;
        MOVI $97FF,r0    ; init data pointer
        MOVI $9BFF,r1    ; init status pointer
;
        MOVI 0,r2        ; init x sum
;
; *******                                                    ********
        jsr sample       ; grab a frame !!! goes to cornea
; *******                                                    ********
;
Cornea: sta disabl       ; disable digitizer
;
        ldy #0           ; load y with 0 so pseudo absolute indirect will work
;
proc:   jsr GetSta       ; get status
;
        bmi Lbr1         ; at end of data in frame so goto EndFram
        bpl cont2
Lbr1:   jmp EndFram
;
cont2:  asl a            ; shift Y/X bit into N flag
        bmi endlin       ; if set then at end of line
;
        asl a            ; shift hi begin/hi end bit into N flag
        bmi beg          ; if we have x begin then goto beg
;
xend:   jsr GetDat       ; else get data and do x end stuff
        sta tmp          ;   store x end
        lda xstat
        bmi en.1
        lda tmp
        sta tmpXE
        lda #$FF
        sta flag         ; and set the flag that endfram will look at
        sta xstat
en.1:   BRA proc         ;  and get some more data
```

```
;
beg:     jsr GetDat        ; get some data ( oh my ! )
         sta tmp
         lda xstat
         bmi bg.1
         lda tmp
         sta tmpXB         ; store x begin
bg.1:    BRA proc          ; get next staus nybble
;
; ********    Endlin : called at end of every line in pass1 *******
;
Endlin:  jsr getdat        ; get y value
         sta ytemp         ;
;
         lda oldy
         cmp #00
         beq spo.2         ; if oldy = 0 then let oldy=ytemp
;
spot1:   sec
         lda Ytemp
         sbc Oldy
         cmp #$01          ; IF this line is contiguous with the last one
                           ;    then add in its x vals ELSE ignore it.
                           ; i.e. we only look at the first hi lev spot.
         bne end1
spo.2:   ADDB r2,tmpxb     ; add x begin to running hi lev x sum
         ADDB r2,tmpxe     ;   etc ...
         inc numx          ; number of x vals used to find x center
         inc numx
;
         lda ytemp         ; update ytemp value
         sta oldy
         sta ycen          ; cornea y cen
end1:    lda #00
         sta xstat
         BRA proc
;
; *******    End of EndLin Procedure             *******
;
;
; ********   EndFram Called when the end of frame status bit ******
;        is set. If there is no data in the frame it goes to Pass1.
;        If any of the spots are too high it goes to the top.
;        Otherwise, it computes the x center of the cornea spot and goes
;        to drawbox (ycen found in endlin).
;
EndFram: jsr GetSta        ; MUST see two EOF status bytes in a row
         bmi end.1         ; before we believe we have a real end of frame.
         jsr getsta        ;   eat bogus stat byte
         jsr getdat
         jsr getdat        ; If we don't find two THEN eat the data associated
         jsr getdat        ;   with the wedged status bytes,
         jmp proc          ; and keep analyzing the data in this frame.
;
end.1:   lda flag          ; IF flag.msb is not set THEN
         bmi goFor
         jmp pass1         ; decrement hi reg and sample again
;
goFor:   lda #00           ; ELSE compute cornea x center
         sta result        ;   by dividing the total x sum in R2
         lda numx          ;   by the number of x values used.
         sta divisor
         lda r2
         sta LoDiv
         lda r2+1
         jsr divide
         lda result        ; The result of the division is in result.
         sta xcen          ; Put the result in xcen.
;
;        Now go draw the box around the cornea !!
```

```
;  ********** DrawBox : Draws a box around the cornea spot **************
;       specified by xcen and ycen.
;
DrawBox: lda xcen             ; get xcen
        sec
        sbc #XRect            ;       compute BoxXB
        sta BoxXB
        sta BxBtmp            ; store Box x beg at temp (BoxXb write only)
        lda xcen              ;       get x cen again
        clc
        adc #XRect            ;       compute BoxXE
        sta BoxXE
        sta BXetmp            ;       store at temporary ( boxxe write only reg )
;
        lda ycen              ; get y cen
        sec
        sbc #YRect            ;       compute BoxYB
        sta BoxYB
        sta YBxBtmp           ;       store at temporary
;
        lda ycen              ;       get y cen again
        clc
        adc #$19              ;       compute BoxYE
        sta BoxYE
        sta YBxEtmp           ;       store at temporary
;
;       clc
;       lda FHiReg            ; get current value of the HiReg
;       adc HiDec             ; add hi decrement value to it
        lda #$40
        sta PrevCor           ;   STORE it at PREVCOR so next sample does not
;                                   have to ramp all the way down.
;
; NOW GO TO PASS 2 --------> OH MY !!!!!!!!!!
;
        sec
        lda PrevLo            ; previous value for loReg in previous grab
        sbc #02
        sta FLoReg            ; Put IniLo in FLoReg so that Pass2 doesn't have to
;                                   ramp Lo threshold up from IniLo.
        jmp top2
;************ END of DrawBox                                  **********
;
;       Kludge - gets called when an invalid state has occured
;       because of invalid digitizer data. It throws away all the
;       data on the current line and resets the state of the
;       pass 2 processing.
;
KLUDGE: lda #0
        sta state             ; reset state
        sta Ystat             ; reset y status
        inc errcnt            ; increment error count
;
        INCR r0               ; inc data pointer
;
loop8:  jsr GetSta            ; get next status byte
        bmi Lbr20             ; if EOF then go to enfrm2
        bpl cont20
Lbr20:  jmp Enfrm2
;
cont20: asl a                 ; shift Y/X but into N flag
        bmi Yval              ; IF set then we have a y value
        INCR r0               ; ELSE inc data pointer and get next status
        BRA loop8
;
Yval:   INCR r0               ; inc data pointer
        jmp proc2             ; continue normal processing of data
;
;       END OF KLUDGE
;
```

```
;**********************************************************************
;********* THIS MARKS THE BEGINNING OF THE PASS2 CODE !!!! ******
;**********************************************************************
;
;       The OR of the state byte and the status byte is put in
;       the X register which then indexes into the following table.
;
tbl:    .addr kludge, LoEnd, HiEnd, kludge
        .addr LoBeg, kludge, LBgHe, kludge
        .addr HiBeg, HBgLe, kludge
;
top2:
Pass2:  clc
        lda FLoReg
        adc #LoInc         ; increment lo register
        cmp #MaxLo         ; lo register to high ?
        bcc cont8          ; no --> continue
        jmp top            ; yes ---> start at top ( pass1 )
;
cont8:  sta LoReg
        sta FLoReg         ; store new loreg value
;
        lda #0
        sta oldy           ; init oldy ( used in eol2 )
        sta state          ; init state
        sta YStat          ; init y status
        sta YHiBg          ; init first line with hi lev on ( y val )
;
        sta errcnt         ; init error count
        sta YcntHi         ; init y count for hi level
        sta YCntLo         ; init lo lev # of lines count
        sta widcnt
        sta widstat
;
        sta HYtmp          ; init Hi lev y tmp (used in eol2, cornea streaking)
;
        MOVI 0,r2          ; Init Y value sum
        MOVI 0,r3          ; init hi lev x sums
        MOVI 0,r4          ; init running midline sum
;
        MOVI $97FF,r0      ; init pointer to image data
        MOVI $9BFF,r1      ; init pointer to status info
;
; end init pointer registers
;
        NOW Sample a Frame !!!!
;
        jsr Sample
;
Pupil:  sta disabl         ; disable digitizer
        ldy #0             ; load y with zero so pseudo abs indirect will work
;
proc2:  jsr GetSta         ; get next status byte
        bmi Lbr16          ; go to end of frame proc
        bpl cont16         ; always branches
Lbr16:  jmp Enfrm2
;
cont16: asl a              ; shift y/x bit into N bit
        bmi Lbr14          ; if set then go to end of line proc
        bpl cont15         ;   always branches
Lbr14:  jmp Eol2
;
cont15: lsr a              ; set up status nybble
        lsr a              ; so we can use it to index into table
        and #%00011000     ; and with mask
;
        ora state          ; or in the state of pass2 processing.
```

```
                tax
                lda tbl,x
                sta vector        ; store lo byte of jump vector
                lda tbl+1,x
                sta vector+1      ; store hi byte of jump vector
                jmp (vector)      ; jump to processing of an x value
;
; *****         LoBeg - handles the x value for a Lo level begin
;
; Side Effects/Changes: tmpxb, state
;
LoBeg:          jsr GetDat        ; get next data byte
                sta tmpXb         ; store it at temp x begin
;
done:           lda #%00000010
                sta state         ; set state so we know we have a lo begin
                jmp proc2         ; get more data
;
;
; ******        Hibeg - handles x hi begin value
;
; Side Effects/Changes: HtmpXB
;                       state
;
HiBeg:          jsr Getdat        ; get next data byte
                sta HtmpXB        ; store it at temp x begin
                lda #%00000100
                sta state         ; set state so that we know we have found a hi begin
                jmp proc2         ; go get more data
;
; ******        HiEND - processes hi level x end value
;
; Side Effects/Changes: HtmpXE, LXend, FstBg (filling in lo lev around cornea)
;                       state, Ystat
;
Hiend:          lda Ystat         ; get the y status of this line
                ora #%01000000    ; set the bit that says there is a hi lev spot on line
                sta YStat
;
                jsr Getdat        ; get next data byte
                sta HtmpXE        ; store at Hi temp x end
                sta LXend         ; store it at last x val for this line (we are filling
                                  ;    in around the cornea spot)
;
;
                lda FstBg
                cmp #00           ; If FStBG=0 THEN store HtmpXB as first x val on this
                bne Hi.foo        ; line (because we are filling in Lo levs around the
                lda HtmpXB        ; cornea so that pupxcen calculation is more accurate)
                sta FstBg
;
Hi.foo:         lda #0
                sta state         ; reset state info
                jmp proc2         ; get more data !!!! oh my ! haaaaaa
;
;               HBgLe - processes x value that is simultaneously
;        a hi begin and a lo end.
; Side Effects/Alters: tmpxe, HtmpXB
;                      Ystat, state
;
HBgLe:          jsr GetDat        ; get some data
                sta tmpXe
;
                lda Ystat
                ora #%10000000    ; set flag so eol knows there is a Lo lev on this line
                sta Ystat
;
                lda tmpXE
```

```
        sta HtmpXB      ; remember HBg/LE ... set h beg
        lda #%00000100
        sta state       ; set state ... we have a Hi begin
        jmp proc2       ; get even more data
;
;       LBgHe - processes X value that is a lo begin and hi end
;       value simultaneously.
;
; Side Effects/Alters: tmpXb, HtmpXE, FstBg
;                      Ystat, state, LoStat
;
LBgHe:  lda Ystat       ; get the y status of this line
        ora #%01000000  ; set the bit that says there is a hi lev spot on line
        sta YStat
        lda #%00000010
        sta state       ; reset state ... we have a lo begin
;
        jsr Getdat      ; get next data byte
        jmp proc2       ;######## TEST ONLY #########
;
done.1: jmp proc2       ; yes friends ... get more data
;
;       Eol2 - processes data at the end of a line
;
; Side Effects/Alters: YTemp, oldy, YCntHi, r5 (temp), YcntLo
;       YHiBg, HYtmp, r3 (hi x sums), r4 (midline running sum)
;                   r2 (Lo Lev Y sums) state, Lostat,Ystat
;
Eol2:   lda #0
        sta state       ; reset state
;
        jsr Getdat
        sta Ytemp       ; store y value in temp
;
;K ***  Begin Fault Tolerant Code  ***
;
;       cmp oldy        ; if current y val > oldy then continue
;       beq LBr21       ;    ----> ELSE goto Enfrm2
;       bcc LBr21       ;
;
;       bcs go.21       ; if we get here then we will always branch to go.21
;
;LBr21: jmp enfrm2      ; jump to end of frame @pass2
;
;go.21: cmp YBxBtmp     ; compare with box y begin
;       bcs go.3        ; if ytemp >= ybxbtmp then continue
;       jmp enfrm2      ;      ELSE jump to end frame pass2
;go.3:  cmp YBxEtmp     ; compare with y box end temp
;       beq go.4        ; IF  eq to ybxe THEN continue
;       bcc go.4        ;   OR if < ybxe THEN continue
;       jmp enfrm2      ;      ELSE jump to end frame pass2
;;
;;K *** End of Fault Tolerant Code ***
;
go.4:   sta oldy        ; put current y value into Oldy
;
        lda Ystat
        bpl HiSpot      ; if no lo lev flag then go to hi spot
;
;------ Process LoLev Data on this line. ------------
;
go.41:
cont.10:sec
        lda LXend       ; last x val on this line (that got through Lo pass)
        sbc FstBg       ; first x val on this line (that got through Lo pass)
        sta r5          ; r5, now holds the hi passed width of this line
;Now use the Lo Pass filter with the higher break frequency (i.e. ignore
;       lines with width less than "XMidFilt")
```

```
;
        cmp #XMidFilt   ;
        bcc YLo.1       ; IF width less than XmidFilt go work on y's
;                         ELSE add proper value to midline running sum
MidVect:sec
        lda FstBg       ; get first x val on this line
        sbc BxBtmp      ; subtract the x val for the box begin
        sta r5+1        ;   store result at a temporary location
;
        lda r5          ; get pseudo width of this line
        lsr a           ; divide it by two
        clc
        adc r5+1        ;
        sta r5+1        ; temporary
        ADDB r4,r5+1    ; add midpoint value to midpoint running sum
;
;       Now deal with Yval running sum (R2)
;
YLo.1:  inc YcntLo      ; increment number of lines that contain
                        ;legitimate filtered data (i.e. height,numX)
        sec
        lda Ytemp       ; current y value
        sbc YBxBtmp     ; subtract YBox Begin (i.e. normalize)
        sta r5+1        ; temporary
        ADDB r2,r5+1    ; add current y value to y val running sum
;
        lda #0
        sta FstBg       ; zero First X Begin
        sta widstat
;
;------- Process Hi Lev Data on this line ------------
;
HiSpot: lda Ystat
        asl a           ; shift hi lev ystat bit into N flag
        bmi hspot
        lda #0
        sta Ystat       ; reset YStat
        jmp proc2
;
Hspot:  lda HYTmp
        cmp #0
        beq new2b       ; if first hi y then store it at HYtmp
;
; the following code was added to account for cornea streaking
        clc
        lda HYtmp
        adc #01
        cmp Ytemp       ; add hi x vals for the first contiguous hi spot only
        bne noAdd
        sta HYtmp       ; maintain Hi Y temp
        ADDB r3,HTmpXB  ; maintain hi x sums
        ADDB r3,HTmpXE
;
        inc YCntHi      ; increment the # of Hi lev pairs count
;
NoAdd:  lda #0
        sta Ystat       ; reset ystat
        sta FstBg       ; first x val on a line
        jmp proc2
;
New2B:  lda Ytemp
        sta HYtmp
        sta YHiBg       ; holds y pos of first line with Hi lev data on it
;
        ADDB r3,HtmpXb  ; add hi x beg to running sum
        ADDB r3,HtmpXe  ; add hi x end to running sum
;
        inc YCntHi      ; increment the # of Hi lev pairs count
```

```
        lda #0
        sta Ystat       ; reset ystat
        sta FstBg       ; first x val on a line
        jmp proc2
;
;       EnFrm2 - Crunches data after pass2 is at end of frame
;
;       Decides when to stop ramping up Lo Reg.
;       Computes X and Y centers of Pupil and cornea. Computes
;       X and Y diff.
;
; Side Effects/Alters: r6 (ydiff,xdiff), pupxcen, pupycen, corxcen
;                      corycen, r7 (gets a * b), PupWid
;
EnFrm2:
;
;   *** Begin Bag Tolerant Code ***
;
        jsr GetSta      ; get next status byte
        bmi go.2        ; if it is also an EOF THEN analyze the frame
;                                ELSE ....
        jsr GetDat      ; "Kill my data" - Eddie Murphy
        jsr GetDat      ;      "Kill my data .."
        jmp proc2       ; and continue processing the frame
;
; *** End Bag Tolerant Code ***
;
;
go.2:
HiLev0: lda ycnthi
        cmp #0          ; if y count hi is zero then we have no hi lev spot
        bne ChkLo
        jmp top         ;       start over
;
ChkLo:
;---------- Decide whether to stop or to inc Lo Reg ----------------
;
        lda widcnt
        cmp #StopVal    ; stop if YcntLo > ??
        bcs winfin
;
go.2a:  jmp top2        ;       ELSE incr lo reg
;
;-------------------------------------------------------------------
;       At this point we think we have a pupil so calc centers
;
;---------------- Find Y Centers -----------------------------------
;
winfin: lda FloReg
        sta PrevLo      ; update prevLo so on next pass we wont ramp
                        ; up from IniLo
        lda YCntHi      ; get height of cornea spot
        lsr a           ; divide by two
        clc
        adc YHiBg       ; add it to first line with a Hi lev on it
        sta CorYCen     ; store cornea Y center
;
;       Compute pupil Y center
;
        lda #0
        sta result      ; zero result for divide routine
        lda YcntLo
        sta divisor     ; put Ycntlo at divisor for divide routine
        lda r2
        sta LoDiv       ;put Lo byte of Ysum at LoDiv
        lda r2+1        ; put hi byte in AC
;
        jsr divide      ; DO the divide (16x8)
        clc
```

```
        lda result          ; get the result of the division
        adc YbxBtmp         ; add box Y begin to it (UNnormalize)
        sta PupYcen         ;Pupil Y center
;
; Now compute Y difference
;
        sec
        lda CorYCen         ; cornea y center
        sbc PupYCen         ; pupil y center
        sta r6              ; store at r6 (y diff)
;
;       Make sure Y Diff is a reasonable value.
;
        cmp #$30            ; IF Y diff < $30 THEN
        bcc go.22           ;    Continue normally.
        cmp #$f6            ; ELSE IF Y diff >= $f6 THEN
        bcs makzer          ;    force ydiff to be zero
        jmp top             ; ELSE start at the top
;
makzer: lda #00
        sta r6              ; put a zero in ydiff (i.e. IF ydiff f6-ff THEN put a
;                    zero in for ydiff) makes it easier for top level.
;
;-------- Compute Cornea X Center --------------------------------
;
go.22:  lda ycnthi          ; get number of hi lev lines
        asl a               ; multiply by 2
        sta divisor         ; store at divisor
        lda r3              ; get lo byte hi x sum
        sta LoDiv           ; store it at lo div
        lda #0
        sta result
        lda r3+1            ; put hi byte of dividend in AC
        jsr Divide          ; DO THE DIVISION !!
        lda result
        sta CorXCen         ; store hi level x center ;-------------- Compute Pupil X Center ---------------------------
;
        lda #0
        sta result          ; zero result
        lda YCntLo          ; get the number of lo lev lines count
        sta divisor
;
        lda r4              ; lo byte of midline values sum
        sta LoDiv           ; set up for (16x8) divide
        lda r4+1            ; hi byte of midline values sum
        jsr Divide          ; do the division. result is Avg of lo x midline values
;
        clc
        lda result
        adc BxBtmp          ; add Box X begin value to Normalized Avg midline vals
        sta PupXCen         ; store lo lev X center
;
;------ Now calculate x difference -----------------
;
        sec
        lda CorXCen         ; get hi x center
        sbc PupXCen         ; subtract lo x center
        sta r6+1            ; store it at r6 + 1 (X diff)
;
;       Hey johnnies , now we return.
;                    HAAAAAAAAAAAAAAAAAAAAAAAAAAAAAAA !!!!! ( JC )
;
        DM.Bell 0, 1        ; beep bell (auditory feedback for the user)
        DM.Wait
;
;;      CAll CrLf
```

```
;;      lda r6              ; y diff
;;      Call NUmout
;;      Call Blank2
;;      lda r6+1            ; x diff
;;      Call Numout
;
;       call blank2
;       lda corxcen
;       call numout
;       call blank2
;       lda pupxcen
;       call numout
;
;       sta enabl           ; use for testing purposes only
;       PAUSE 30            ;   pauses for .3 seconds
;       sta disabl
;
        lda #$FF            ; hack to zero Z flag (to indicate no esc key pressed)
        rts
;       jmp top.1           ; for testing only
;
;
;***********************************************************************
;*******                                                         *******
;*******         THE FOLLOWING ROUTINES ARE SUBROUTINES USED     *******
;*******                BY THE EYETRACKING MODULE                *******
;***********************************************************************
;
;
;*********** Divide : A general 16bit by 8bit division ************
;
;       routine. Takes divisor in Divisor (0 page addr).
;       High byte of dividend in AC. Lo byte in LoDiv.
;       Puts result in Result and remainder in AC.
;
Divide: tsx
        stx stack
        ldy #8
        sec
        sbc divisor
loop1:  php
        rol result
        asl LoDiv
        rol a
        plp
        bcc add
        sbc divisor
        BRA next
add:    adc divisor
next:   dey
        bne loop1
        bcs last
        adc divisor
        clc
last:   rol result
;
        ldx stack
        txs
        rts                 ; return
;
; ********* End of Divide                    ***************
;
;
;       GetDat : Gets the next data byte of the video
;       frame data. Uses R0 as a pointer to the next byte of data.
;
GetDat: INCR r0             ; increment pointer
        lda (r0),y          ; get next data byte
        rts                 ; return from subroutine
```

```
;       GetSta : Gets the next status byte of the video frame data.
;               Uses R1 as a pointer to the next status byte.
;
GetSta: INCR r1            ; increment pointer
        lda (r1),y         ; get next status byte ( note: only hi nybble useful )
        rts                ; return from subroutine ; ******           SAMPLE                  *************
;
;       This routine enables the video digitizer and waits for
;       it to tell the aim that is done sampling a frame of data.
;       Polling is the technique used.
;
Sample: sta enabl          ; enable digitizer
loop2:  lda VipSta         ; poll VIP
        bmi loop2          ; if hi then digitizer busy
        ldx #$10
bag.1:  dex
        cpx #00            ; if x = 0 THEN return
        bne bag.1
        rts                ; return ; complement - this routine complements r2 (sixteen bits)
;
Cpl:    sec
        lda #0
        sbc r2
        sta r2
        lda #0
        sbc r2+1
        sta r2+1
;
        rts
;
; mult - this routine multiplies "a" (minor axis) times "b" (major axis) and
;        puts the result in R7.
;
;mult:  MOVI 0,r7          ; zero reg
;
;ldx PupWid                ; when this routine is called PupWid contains "b"
;loop.d:       ADDB r7,r5  ; ycntlo/2=height/2="a" is in r5
;       dex
;       cpx #0
;       bne loop.d
;       rts
;
        .end start
```

What I claimed is:

1. An eye-tracker system comprising:
(a) a light source;
(b) a television camera producing video signals;
(c) a frame encoder circuit connected to the video signal output from the camera for encoding the signals at at least two threshold levels and storing said encoded data for a two dimensional area within said frame in a cache memory, said threshold levels being programmable; and
(d) a computer in communication with said encoder circuit at least via its data bus and address bus for programming said threshold levels, controlling the encoder and accessing data in said cache memory;
(e) said computer having an associated main memory with a stored task for reading the cache memory and interactively controlling the frame encoder including a subtask for finding the corneal reflection of an eye upon which the camera is focussed by lowering the upper threshold until the brightest spot on the frame is detected and having a subtask for finding the pupil of the eye by raising the lower threshold at least until the border between the pupil and the iris of the eye upon which the camera is focussed is defined and having a third subtask for finding the center of the corneal reflection and the center of the pupil and establishing the vector from the center of the corneal reflection to the center of the pupil.

2. An eye-tracker communication system comprising:
(a) a display bearing indicia which may be selected by a user with one of the user's eyes;
(b) a light source;
(c) a television camera producing video signals, said television camera and light source arranged to be focussed upon the eye of a user facing the display;
(d) a frame encoder circuit connected to the video signal output from the camera for encoding the signals at at least two threshold levels and storing said encoded data for a two dimensional area within said frame in a cache memory, said threshold levels being programmable; and (e) a computer in communication with said encoder circuit at least via its data bus and address bus for programming said threshold levels, controlling the encoder and accessing data in said cache memory;

(f) said computer having an associated main memory with (i) a stored task for reading the cache memory and interactively controlling the frame encoder including a subtask for finding the corneal reflection of an eye upon which the camera may be focussed by lowering the upper threshold until the brightest spot on the frame is detected and having a subtask for finding the pupil by raising the lower threshold at least until the border between the pupil and the iris of the eye upon which the camera may be focussed is defined and having a third subtask for finding the center of the corneal reflection and the center of the pupil and establishing the vector from the center of the corneal reflection to the center of the pupil; and (ii) a task for correlating the vector with the indicia upon the display and outputting a signal indicative of the indicia selected by a user.

* * * * *